United States Patent [19]

Michalko

[11] 4,107,086
[45] Aug. 15, 1978

[54] CATALYTIC COMPOSITE AND METHOD OF MANUFACTURE

[75] Inventor: Edward Michalko, Chicago, Ill.

[73] Assignee: UOP Inc., Des Plaines, Ill.

[21] Appl. No.: 786,524

[22] Filed: Apr. 11, 1977

Related U.S. Application Data

[63] Continuation-in-part of Ser. No. 671,893, Mar. 29, 1976, abandoned, and a continuation-in-part of Ser. No. 671,895, Mar. 29, 1976, abandoned.

[51] Int. Cl.$^2$ .................... B01J 29/06; C07C 3/00; C07C 3/58
[52] U.S. Cl. ..................... 252/455 Z; 260/672 T
[58] Field of Search ............... 252/455 Z; 260/672 T

[56] References Cited

U.S. PATENT DOCUMENTS

| | | | |
|---|---|---|---|
| 3,531,397 | 9/1970 | Michalko | 252/455 Z |
| 3,781,199 | 12/1973 | Ward | 208/89 |
| 3,794,598 | 2/1974 | Schlaffer | 252/455 Z |
| 4,039,479 | 8/1977 | Gembicki et al. | 252/455 Z |

*Primary Examiner*—Carl F. Dees
*Attorney, Agent, or Firm*—James R. Hoatson, Jr.; Robert W. Welch; William H. Page, II

[57] ABSTRACT

A catalytic composite of improved activity and a method of manufacture is disclosed. The catalytic composite is particularly effective with respect to the transalkylation of toluene. The catalytic composite comprises a zeolite of the mordenite crystal structure in from about a 1:3 to about a 3:1 weight ratio with a refractory inorganic oxide. The catalytic composite is characterized by a method of preparation which comprises subjecting zeolite of the mordenite crystal structure, with a sodium content of less than about 5 wt. % as $Na_2O$, to an aqueous ammoniacal treatment at a pH of at least about 9.5, and thereafter admixing said zeolite with said refractory inorganic oxide.

18 Claims, No Drawings

4,107,086

CATALYTIC COMPOSITE AND METHOD OF MANUFACTURE

CROSS-REFERENCE TO RELATED APPLICATIONS

This application is a continuation-in-part of a copending application Ser. No. 671,895, filed Mar. 29, 1976, and a copending application Ser. No. 671,893, filed Mar. 29, 1976 both said applications being now abandoned.

Crystalline aluminosilicates, or zeolites, of which mordenite is one example, are well known in the art and have found extensive application as hydrocarbon conversion catalysts or as a component thereof. Such materials are of ordered crystalline structure often visualized as a three-dimensional network of fundamental structural units consisting of silicon-centered $SiO_4$ and aluminum-centered $AlO_4$ tetrahedra, the tetrahedra being interconnected by a mutual sharing of apical oxygen atoms and arranged to form cages or cavities in open communication through smaller intracrystalline channels or pore openings whose narrowest cross section has essentially a uniform diameter characteristic of each crystalline aluminosilicate variety. To effect a chemical balance, each $AlO_4$ tetrahedra has a cation associated therewith — usually a sodium or other exchangeable cation. The aforementioned cages or cavities are occupied by water molecules and by the last mentioned cations, both of which exhibit considerable freedom of movement permitting ion-exchange and reversable dehydration.

The crystalline aluminosilicates, or zeolites, employed in the manufacture of the catalytic composite of this invention, are of the mordenite crystal structure, highly siliceous in nature and generally characterized by a silica-alumina mole ratio of from about 6 to about 12 as found in nature. The mordenite crystal structure comprises four- and five-membered rings of the $SiO_4$ and $AlO_4$ tetrahedra so arranged that the crystal lattice comprises pores and channels running parallel along the crystal axis to give a tubular configuration. This structure is unique among the crystalline aluminosilicates since the channels or tubes do not intersect, and access to the cages or cavities is in only one direction. For this reason, the mordenite structure is frequently referred to as two-dimensional. This is in contrast to other well-known crystalline aluminosilicates, for example faujasite, in which the cavities can be entered from three directions. Mordenite, clinoptilolite, or mordenite which has been synthesized or acid extracted, caustic extracted or otherwise treated to increase the silica-alumina mole ratio to about 20:1 or more while maintaining the mordenite crystal structure, may be used in the manufacture of the catalytic composite of this invention.

Crystalline aluminosilicates having a mordenite crystal structure have heretofore been utilized composited with a refractory inorganic oxide, typically alumina, as a hydrocarbon conversion catalyst, and are particularly useful with respect to the transalkylation of alkylaromatic hydrocarbons. It is an object of this invention to present a new and useful method of manufacture providing a novel catalytic composite of improved activity.

In one of its broad aspects, the present invention embodies a method of manufacture providing a catalytic composite of improved activity which comprises subjecting a zeolite of the mordenite crystal structure and containing less than about 5 wt. % sodium, calculated as $Na_2O$, to an aqueous ammoniacal treatment at a pH of at least about 9.5, and thereafter admixing said zeolite with a refractory inorganic oxide in a weight ratio of from about 1:3 to about 3:1, and calcining the mixture to provide said catalytic composite.

Another embodiment of this invention concerns a catalytic composite comprising a calcined mixture of a refractory inorganic oxide and a zeolite of the mordenite crystal structure, said zeolite having been treated with an aqueous ammoniacal base solution at a pH of at least about 9.5 while containing less than about 5 wt. % sodium, calculated as $Na_2O$, and thereafter admixed with said refractory inorganic oxide in a weight ratio of from about 1:3 to about 3:1 and calcined to provide said catalytic composite.

One of the more specific embodiments relates to a method of manufacture providing a catalytic composite of improved activity which comprises subjecting a zeolite of the mordenite crystal structure and containing less than about 5 wt. % sodium, calculated as $Na_2O$, to an aqueous ammoniacal treatment at a pH of from about 10 to about 12, and thereafter admixing said zeolite with alumina, and calcining the mixture to provide said catalytic composite.

A still more specific embodiment is in a method of manufacture providing a catalytic composite of improved activity which comprises subjecting mordenite, containing less than about 5 wt. % sodium, calculated as $Na_2O$, to an aqueous ammoniacal treatment with a pH of from about 10 to about 12 and at a temperature of from about 75° to about 200° C., and thereafter admixing said mordenite with an alpha-alumina monohydrate, and calcining the mixture to provide said catalytic composite.

A still further embodiment of the present invention relates to a catalytic composite comprising a calcined mixture of an alumina and mordenite, said mordenite having been treated with an aqueous ammoniacal base solution at a pH of from about 10 to about 12 and at a temperature of from about 75° to about 200° C. while containing less than about 5 wt. % sodium, calculated as $Na_2O$, and thereafter admixed with an alpha-alumina monohydrate in a weight ratio of from about 1:3 to about 3:1 and calcined to provide said catalytic composite.

Other objects and embodiments of this invention will become apparent in the following detailed specification.

Pursuant to the present invention, the zeolite is subjected to an aqueous ammoniacal treatment at a pH of at least about 9.5 prior to admixture with the refractory inorganic oxide. The aqueous ammoniacal treatment can be effected at a temperature of from about 75° to about 200° C. over a period of from about 1 to about 24 hours. The treatment can be effected at substantially atmospheric pressure in an open vessel at about the reflux temperature of the aqueous ammoniacal solution albeit over a more extended period up to about 24 hours. The treatment is effective over a substantially shorter period, say from about 1 to about 10 hours at autogenous pressures utilizing a closed vessel. Suitable ammoniacal solutions include solutions of bases such as ammonium hydroxide, hydroxylamine, hydrazine, tetramethylammonium hydroxide, etc., or strong organic amines like methylamine, dimethylamine, ethylamine, diethylamine, propylamine, diisopropylamine, n-butylamine, t-butylamine, diisobutylamine, n-amylamine, n-hexylamine, ethylene diamine, hexamethylenediamine, benzylamine, aniline, piperazine, piperadine, and the like, the selected base being employed in sufficient concentration to provide a pH of at least about 9.5, and preferably from about 10 to about 12.

The crystalline aluminosilicate, or zeolite, employed herein as a starting material should contain, or should be treated to contain, less than about 5 wt. % sodium calculated as Na$_2$O. The sodium can be reduced to an acceptable level by conventional and widely practiced ion-exchange techniques. Typically, ammonium cations are exchanged for sodium cations on treating the zeolite in contact with the aqueous ammonium salt solution, for example an aqueous ammonium chloride solution. The resulting ammonium-exchanged zeolite is thereafter heat-treated to effect thermal decomposition of the ammonium cations and formation of the hydrogen form of the zeolite. In any case, the treatment may be effected one or more times to reduce the sodium content to less than about 5 wt. % calculated as Na$_2$O.

Refractory inorganic oxides for use in accordance with the method of this invention include the naturally occurring as well as the synthetically prepared refractory inorganic oxides. Suitable refractory inorganic oxides are such as alumina, silica, zirconia, titania, thoria, boria, magnesia, chromia, stannic oxide, and the like, as well as combinations and composites thereof, for example, alumina-silica, alumina-zirconia, alumina-titania, etc. Alumina is a preferred refractory inorganic oxide for use herein, particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred.

The treated zeolite may be combined in intimate admixture with the refractory inorganic oxide in any conventional or otherwise convenient manner. For example, the treated zeolite can be admixed with an alumina precursor subsequently converted to alumina to provide the zeolite in intimate admixture with the alumina. The treated zeolite may be commingled with an acidic alumina sol, such as results from digesting aluminum in hydrochloric acid under controlled conditions, provided that the treated zeolite is not unduly exposed to the acidic media, the mixture being thereafter treated at conditions effecting gelation of the sol. For example, the mixture can be dispersed as droplets in a hot oil bath whereby gelation occurs with the formation of spheroidal gel particles substantially in accordance with the method of U.S. Pat. No. 2,620,314. In this instance, the treated zeolite is conveniently and advantageously commingled with an aqueous methylenetetramine (HMT) solution before being admixed with the acidic sol, the HMT otherwise serving as a buffering agent in accordance with the teaching of said patent. In this manner, at least a portion of the HMT solution becomes occuded in the treated zeolite to assure a less acid environment in the immediate vicinity of the zeolite during the critical period in which the acid anion content of the sol is substantially neutralized by the buffering action of the HMT to promote a progressive gelation of the sol. One preferred method comprises commingling the zeolite with a powdered refractory inorganic oxide, adding a binder and/or lubricant to the mixture, and compressing the mixture into pills or pellets of uniform size and shape. Alternatively, and still more preferably, the treated zeolite is mulled with a powdered form of the refractory inorganic oxide, and with a peptizing agent such as nitric acid, to form an extrudable dough. The dough can be pressured through a die of predetermined size to form extrudate articles utilized as such or rolled into spheres in a spinning drum prior to calcination. The zeolite is preferably calcined in intimate admixture with the selected refractory inorganic oxide in a weight ratio of from about 1:3 to about 3:1.

In any case, the treated zeolite is calcined in admixture with the refractory inorganic oxide to form a catalytic composite. Calcination is suitably in an air atmosphere at a temperature of from about 425° to about 750° C., preferably at a temperature of from about 475° to about 550° C., over a period of from about 0.5 to about 10 hours.

The catalytic composite of this invention is particularly useful for the transalkylation of alkylaromatic hydrocarbons. Thus, an alkyl-aromatic hydrocarbon having from about 7 to about 15 carbon atoms per molecule is treated at transalkylation conditions including a temperature of from about 200° to about 480° C. and a pressure of from about atmospheric to about 1500 pounds per square inch guage (psig) in contact with a catalyst comprising essentially the catalytic composite of this invention to form products of higher and lower number of carbon atoms than said alkylaromatic hydrocarbon. The preferred composition employed as the catalytic composite comprises mordenite in admixture with alumina, said mordenite comprising from about 25 to about 75 wt. % of said composite.

The alkylaromatic hydrocarbon feed stock can be a substantially pure alkylaromatic hydrocarbon of from about 7 to about 15 carbon atoms, a mixture of such alkylaromatic hydrocarbons, or a hydrocarbon fraction rich in said alkylaromatics. Suitable alkylaromatic hydrocarbons include alkylbenzenes and alkylnaphthalenes, preferably with an alkyl group of less than about 4 carbon atoms. The catalytic composite is particularly effective in the treatment of the more difficulty transalkylatable toluene to form benzene, xylenes, or other polymethylbenzenes.

The transalkylation, or disproportionation, reaction can be effected in contact with the catalytic composite of this invention in any conventional or otherwise convenient manner and may comprise a batch or continuous type of operation. A preferred type of operation is of the continuous type. For example, the above described catalyst is disposed in a fixed bed in a reaction zone of a vertical tubular reactor and the alkylaromatic feed stock charged in an upflow or downflow manner, the reaction zone being maintained at a temperature of from about 200° to about 480° C., preferably at a temperature of from about 220° to about 460° C. Although pressure does not appear to be an important variable with respect to the transalkylation reaction of this invention, the process is generally conducted in the presence of an imposed hydrogen pressure to provide from about 1 to about 10 moles of hydrogen per mole of hydrocarbon. However, there is no net consumption of hydrogen in the process, and the hydrogen charge is recovered from the reactor effluent and recycled.

The transalkylation reaction can be effected over a wide range of space velocities. In general, the process is conducted at a space velocity of from about 0.2 to about 10. Space velocities herein referred to are liquid hourly space velocities, (LHSV) i.e., volume of charge per volume of catalyst per hour. While the catalytic composite prepared by the present method permits unusually high space velocities indicative of high activity, the catalytic composite is particularly noteworthy because of its relatively high stability at a high activity level.

The composite prepared in accordance with the method of this invention may be employed as a component of a catalyst comprising any of the several catalytically active metallic materials in the oxidized or reduced state. Of particular interest are those catalytic composites comprising one or more metals of Group VIB and VIII including molybdenum, tungsten, chromium, iron, nickel, cobalt, platinum, palladium, ruthenium, rhodium, osmium and iridium. Thus, the composite of this invention can be utilized advantageously as a catalyst or component thereof to effect a variety of hydrocarbon conversion reactions involving reaction conditions comprising a temperature in the 25°–760° C. range. The catalysts are particularly useful in effecting the hydrocracking of heavy oils, including vacuum residuals, to form petroleum products in the middle distillate range utilizing a temperature of from about 260° to about 1560° C. and pressures of from about 500 to about 1000 psig. Said hydrocarbon conversion reactions further include polymerization of olefins, particularly ethylene, propylene, 1-butene, 2-butene, isobutylene and also higher boiling olefins, at polymerization reaction conditions. The composite of this invention is also useful as a catalyst or component thereof in effecting the alkylation of isoparaffins with olefins or other alkylating agents including, for example, alkyl halides and the like; and also the alkylation of isobutane, isopentane, and/or isohexane with ethylene, propylene, 1-butene, etc., or mixtures thereof; and also the alkylation of aromatics with olefins or other alkylating agents, particularly the alkylation of benzene, toluene, etc., with propylene, butylene, and higher boiling olefins, including nonenes, decenes, undecenes, etc., the foregoing alkylation reactions being effected at alkylation conditions disclosed in the art. The composite of this invention is further useful in the isomerization of paraffins, particularly n-butane, n-pentane, n-hexane, n-heptane, n-octane, etc., or mixtures thereof, including isomerization of less highly branched chain saturated hydrocarbons to more highly branched chain saturated hydrocarbons such as the isomerization of 2- or 3-methyl pentane to 2,2- and 2,3-dimethylbutane, isomerization of naphthenes, for example, the isomerization of dimethylcyclopentane to methylcyclohexane, isomerization of methylcyclopentane to cyclohexane, etc., at isomerization reaction conditions. Other hydrocarbon conversion reactions including the reforming of naphtha to gasoline, dehydrogenation of ethylbenzene to styrene, and hydrogenation of benzene to cyclohexane, are effectively catalyzed utilizing the composite of this invention as a catalyst or as a component thereof.

The following examples are presented in illustration of certain preferred embodiments of this invention and are not intended as an undue limitation on the generally braod scope of the invention as set out in the appended claims.

EXAMPLE I

In this example, a catalytic composite of mordenite and alumina was prepared without the benefit of the aqueous ammoniacal treatment herein described. Thus, 595 grams of a commercial mordenite (H Zeolon) containing about 0.16 wt. % sodium as $Na_2O$ and 16 wt. % volatile matter, as evidenced by weight loss on ignition at 900° C., was thoroughly dry-mixed with 694 grams of a commerical alpha-alumina monohydrate (Kaiser medium) containing about 28% volatile matter. Approximately 20 milliliters of concentrated nitric acid and 420 milliliters of water was admixed therewith, and the mixture mulled to form an extrudable dough. The resulting dough was extruded through a 1/16 inch die and the extrudate segmented and balled in a spinning drum with the formation of 1/16-⅛ inch spheroidal particles. The spheroidal product was substantially calcined in air at 500° C. for 1 hour.

EXAMPLE II

The preparation of Example I was repeated except that the mordenite therein described was subjected to an aqueous ammoniacal treatment prior to admixture with the alumina, the mordenite being subsequently calcined in intimate admixture with the alumina. In this example, the mordenite was first immersed in an aqueous solution of ammonium hydroxide containing 5 wt. % $NH_3$ and having a pH of about 11.6. Five volumes of solution were employed per volume of mordenite. The aqueous ammoniacal treatment was effected under reflux conditions utilizing a glass flask equipped with an overhead condenser. The treatment was effected over a 16 hour period at substantially atmospheric pressure conditions, after which the mordenite was recovered and dried. The mordenite was thereafter thoroughly dry-mixed with the alpha-alumina monohydrate to provide a 50-50 weight mixture with 20 milliliters of concentrated nitric acid in 420 milliliters of water being subsequently added. After thorough mulling to provide an extrudable dough, the dough was extruded, segmented, and formed into spheres as heretofore described. The spheroidal product was calcined in air for 1 hour at 500° C. and thereafter evaluated with respect to the transalkylation of toluene in the described manner.

The above-described preparations were evaluated with respect to the transalkylation of toluene. In each case, toluene, in admixture with hydrogen to provide a hydrogen/hydrocarbon mole ratio of about 10, was charged downflow through a 50 cubic centimeter bed of approximately ⅛ inch spheroidal catalyst particles at a liquid hourly space velocity of 2.0, and at transalkylation conditions including a pressure of 500 psig. The temperature of the catalyst bed was adjusted to effect a 40% conversion of a toluene feed stock, the temperature in each case being taken as a measure of catalyst activity.

The catalytic composites of Examples I and II required temperatures of 475° and 380° C., respectively, the latter being prepared according to the method of this invention.

EXAMPLE III

In this example, the mordenite employed was an ammonium ion-exchanged mordenite as opposed to the aqueous ammoniacal solution-treated mordenite of this invention. Thus, a solution of 260 grams of ammonium nitrate in 2340 cubic centimeters of water was used to ammonium ion-exchange 600 grams of the mordenite. The mordenite was slurried in 600 cc portions of the solution of about 55° C. for about ½ hour, the mordenite being recovered by filtration after each of three such ammonium ion-exchange treatments. After the final treatment the mordenite was dried at about 95° C. The mordenite was thereafter thoroughly dry-mixed with the alpha-alumina monohydrate to provide a 50-50 weight mixture with 20 milliliters of concentrated nitric acid in 420 milliliters of water being subsequently added. After thorough mulling to provide an extrudable dough, the dough was extruded, segmented and formed into spheres as heretofore described. The spheroidal product was calcined in air for 1 hour at 500° C., and thereafter evaluated with respect to the transalkylation of toluene in the described manner. A 40% conversion was achieved at 463° C.

EXAMPLE IV

A substantially pure mordenite (H Zeolon), in the form of extrudate particles was calcined in air for 1 hour at 500° C. and thereafter evaluated with respect to the transalkylation of toluene in the described manner. In this instance, a temperature of 508° C. was required to achieve a 40% conversion. In a separate experiment, the calcined extrudate was further treated with an aqueous ammoniacal solution. In this instance, the mordenite was sealed in a glass-lined rotating autoclave together with an aqueous ammoniacal solution substantially as described in Example II. The treated mordenite was then further calcined in air at 500° C. for 1 hour. Although the temperature required to effect a 40% conversion of toluene was reduced to 473° C., the temperature is substantially higher than that required when the treated mordenite is calcined in intimate admixture with alumina.

I claim as my invention:

1. A catalytic composite comprising a calcined mixture of a refractory inorganic oxide and a zeolite of the mordenite crystal structure, said zeolite having been treated with an aqueous ammoniacal base solution at a pH of at least about 9.5 while containing less than about 5 wt. % sodium, calculated as $Na_2O$, and thereafter admixed with said refractory inorganic oxide in a weight ratio of from about 1:3 to about 3:1, and calcined to provide said catalytic composite.

2. The catalytic composite of claim 1 further characterized in that said zeolite is mordenite.

3. The catalytic composite of claim 1 further characterized in that said zeolite is clinoptilolite.

4. The catalytic composite of claim 1 further characterized in that said refractory inorganic oxide is alumina.

5. The catalytic composite of claim 1 further characterized in that said refractory inorganic oxide is an alpha-alumina monohydrate.

6. The catalytic composite of claim 1 further characterized in that said mixture is calcined at a temperature of from about 425° to about 750° C.

7. The catalytic composite of claim 1 further characterized in that said mixture is calcined at a temperature of from about 475° to about 550° C.

8. The catalytic composite of claim 1 further characterized in that said aqueous ammonia treatment is effected at a pH of from about 10 to about 12.

9. The catalytic composite of claim 1 further characterized in that said aqueous ammoniacal treatment is effected at a temperature of from about 75° to about 200° C.

10. A method of manufacture providing a catalytic composite of improved activity which comprises subjecting a zeolite of the mordenite crystal structure and containing less than about 5 wt. % sodium, calculated as $Na_2O$, to an aqueous ammoniacal treatment at a pH of at least about 9.5, and thereafter admixing said zeolite with a refractory inorganic oxide in a weight ratio of from about 1:3 to about 3:1, and calcining the mixture to provide said catalytic composite.

11. The method of claim 10 further characterized in that said zeolite is mordenite.

12. The method of claim 10 further characterized in that said zeolite is clinoptilolite.

13. The method of claim 10 further characterized in that said refractory inorganic oxide is alumina.

14. The method of claim 10 further characterized in that said refractory inorganic oxide is an alpha-alumina monohydrate.

15. The method of claim 10 further characterized in that said mixture is calcined at a temperature of from about 425° to about 750° C.

16. The method of claim 10 further characterized in that said mixture is calcined at a temperature of from about 475° to about 550° C.

17. The method of claim 10 further characterized in that said aqueous ammonia treatment is effected at a pH of from about 10 to about 12.

18. The method of claim 10 further characterized in that said aqueous ammoniacal treatment is effected at a temperature of from about 75° to about 200° C.

* * * * *